United States Patent
Sereboff

(10) Patent No.: US 6,237,598 B1
(45) Date of Patent: May 29, 2001

(54) VOLUMIZED APPARATUS FOR TRAUMA MITIGATION AND ASSOCIATED METHOD

(76) Inventor: Joel Sereboff, 2215 Millridge Rd., Owings Mills, MD (US) 21117

( * ) Notice: Subject to any disclaimer, the term of this patent is extended or adjusted under 35 U.S.C. 154(b) by 0 days.

(21) Appl. No.: 09/373,831

(22) Filed: Aug. 13, 1999

(51) Int. Cl.[7] ................................................. A61G 15/00
(52) U.S. Cl. ........................... 128/845; 128/846; 128/882
(58) Field of Search ................................ 128/845, 846, 128/869, 870, 882; 5/654, 909, 455, 450, 457, 458

(56) References Cited

U.S. PATENT DOCUMENTS

| | | |
|---|---|---|
| D. 346,296 | 4/1994 | Sereboff . |
| 4,588,229 | 5/1986 | Jay . |
| 4,761,011 | 8/1988 | Sereboff . |
| 4,896,388 | 1/1990 | Bard . |
| 5,113,540 | 5/1992 | Sereboff . |
| 5,141,489 | 8/1992 | Sereboff . |
| 5,195,199 | 5/1993 | Sereboff . |
| 5,303,977 | 4/1994 | Sereboff . |
| 5,328,246 | 7/1994 | Sereboff . |
| 5,356,099 | 10/1994 | Sereboff . |
| 5,475,882 | 12/1995 | Sereboff . |
| 5,590,430 | 1/1997 | Sereboff . |
| 5,776,088 | 7/1998 | Sereboff . |

*Primary Examiner*—Michael A. Brown
(74) *Attorney, Agent, or Firm*—David C. Jenkins; Arnold B. Silverman; Eckert Seamans Cherin & Mellott, LLC

(57) ABSTRACT

An apparatus is provided which includes a support device secured to a structure. The apparatus comprises first and second chambers containing first and second fluids wherein the resiliency of one of the chambers is lower than the resiliency of the other chamber. The chamber having the lower resiliency is positioned so as to be closer to the body of a user than the other chamber. The support device in the apparatus is secured to a structure which can include but is not limited to, back supports, automobile seats, helmets, casts, cervical collars, automobile air bags, and wrist supports for keyboards and mouse pads. The fluid media used in the support device includes air, liquids, and gels. An additional chamber may be employed between the first and second chambers in the support device to provide stability to the support device. A method for using the support device to support various user body portions is also disclosed.

23 Claims, 5 Drawing Sheets

VOLUMIZED APPARATUS FOR TRAUMA MITIGATION AND ASSOCIATED METHOD

BACKGROUND OF THE INVENTION

1. Field of the Invention

The present invention generally relates to apparatus and methods employed in providing support and reducing trauma for a user. The present invention more particularly relates to an apparatus and associated method utilizing a device in conjunction with a structure to provide support and comfort to the user, preferably a human user.

2. Description of the Prior Art

Support devices for supporting and maintaining parts of the human body generally have been known in the art. One example of a basic type of support device is an air-filled support apparatus which is employed by a driver on an automobile seat to support and comfort the back region of the driver. Automotive manufacturers also currently incorporate adjustable air cushions into automobile seats.

Other types of support devices may be used for holding and/or comforting localized parts of a human user. Air casts are another type of support device which secure and maintain limbs such as broken arms or legs to permit the broken limbs to heal as effectively and efficiently as possible while maximizing the comfort of the user. In addition, support devices which incorporate a fluid such as a gel can further enhance the comfort of a user employing the support device.

Air pillows are another type of support device known in the art. They have been used in a wide variety of applications, including sleeping pillows and cushions for seating.

One of the problems associated with conventional support devices is how to balance and maximize both user comfort and support. Traditional air support devices by their form and design can provide surfaces which generate substantial and uncomfortable reactive forces when providing support in their intimate contact with human users. However, changing this form and design to focus solely on the comfort of the user would result in an apparatus that fails to provide the necessary support function. As a result, a key issue in support device design is how to balance the comfort and support provided to the user.

Another problem associated with conventional support devices arises from the usage of gel or other suitable liquids in the support device. The cost of a support device employing gel or liquids can be relatively high for both the manufacturer and the consumer, and can increase in proportion to the amount of gel or liquid used in the support device. As a result, the capability of the support device to provide comfort and support can be limited by the prohibitive expense of gels and liquids.

U.S. Pat. No. 5,113,540 to Sereboff discloses an example of a fluid cushion. The fluid cushion of this patent includes upper and lower surface members which define a fluid tight housing. Through passages formed in this cushion serve to receive the ischia spine bones of a human user and to minimize the discomfort of a user for prolonged periods of sitting.

U.S. Pat. No. 5,195,199 to Sereboff also discloses a fluid cushion. The fluid cushion of this patent comprises a fluid tight closed housing having an upper surface member, a lower surface member and an intermediate membrane member, which define first and second chambers within the fluid cushion. These first and second chambers each have a fluid medium contained therein. The teaching of this invention provides that the fluid media may have differing viscosities. However, this patent does not teach use of its fluid cushion in conjunction with support structures. Nor does this patent appear to teach minimizing cost considerations while providing comfort and support to the user.

U.S. Pat. No. 5,303,977 to Sereboff discloses a fluid cushion system comprising at least one fluid casing member adapted to be at least partially filled with liquid and formed in a substantially rectangular bag-like contour. The fluid cushion system also comprises a resilient housing for providing structural support for the fluid casing member. The fluid casing member can be inserted into and removed from the original housing.

U.S. Pat. No. 5,475,882 to Sereboff discloses a deformable, low density gel composition comprising a plasticizer having a plurality of particles dispensed therein. The density of the particles is reported as being less than the density of the plasticizer. The gel comprises about 80% weight of the plasticizer and about 20% weight of the particles. This patent also discloses a cushion comprising this gel composition contained in a fluid impervious flexible enclosure. A similar gel deformable low density gel composition is also disclosed in U.S. Pat. No. 5,590,430 to Sereboff.

U.S. Pat. No. 5,356,099 to Sereboff discloses a wrist support system, including a substantially planar and longitudinal support member mounted on a base surface next to a keyboard. A liquid-containing pack is positioned contiguous to an upper surface of the support member for resiliently interfacing in a deformable manner with at least a portion of a user's palm and rest when the user is operating the keyboard. The patent discloses that the wrist support system is provided to alleviate symptoms of carpal tunnel syndrome.

U.S. Pat. No. 5,776,088 to Sereboff discloses a support device comprising a resilient pad member having a viscous substance contained in a flexible member, and a permanently deformable device insertable in the flexible member adjacent to and in influential contact with the viscous substance.

U.S. Pat. No. 5,141,489 to Sereboff discloses a cervical brace for supporting a user's head. The cervical brace comprises a mounting device which includes a thoracic plate and a back plate. A mobilization device is secured to the mounting device which has a rigid chin rest plate with a flexible sheet defining a chin rest pocket. The mobilization device also possesses a rigid head rest plate which has a flexible sheet forming a pocket therein. Resilient pad members are inserted into these pockets to provide a substantially fluid or viscous fluid interface with a chin or head of a user.

U.S. Pat. No. 4,896,388 to Bard discloses a pillow casing. The pillow casing comprises a top surface and a bottom surface which define an opening suitable to receive a compressible filler, or pillow. A thin envelope layer is positioned intermediate at the top and bottom surfaces and attached to the bottom surface. The envelope layer is stated to be adapted to sealably receive a fluid-like material.

U.S. Pat. No. 4,588,229 to Jay discloses a seat cushion for a human user. The seat cushion is stated to include a pad adapted to be used in combination with a shaped tray. The pad comprises a flexible envelope containing a fluid filling material.

None of the above patents teaches the apparatus of the present invention, wherein a first chamber containing a fluid is secured to a support structure and a second chamber is secured to the first chamber. What is not offered in the prior art is a support device with chambers positioned so that the chamber having the lower resiliency is positioned next to the body of the user to provide comfort. The chamber having the higher resiliency is secured to a structure and is separated a distance from the user to provide stability to the support device and to promote user comfort.

What is also needed, therefore, are an apparatus and associated method which employ a volumized, fluid-containing support device designed for use in conjunction with a structure to maximize both comfort and support provided to a human user. What are also needed are an apparatus and method which will maximize economical usage of gels or liquids employed in a functional support device.

SUMMARY OF THE INVENTION

The apparatus and associated methods of the present invention have met or exceeded the above-described needs by providing a support device secured to a structure which offers support and comfort to a user while minimizing the amount of liquid or gel required in the support device.

The apparatus of the present invention comprises a support device which is secured to a structure. The support device further comprises a first fluid contained in a first chamber and a second fluid contained in a second chamber. The fluid in the first chamber may be either air or liquid which provides resiliency to the first chamber. The fluid contained in the second chamber provides a resiliency for the chamber which differs in degree with respect to the resiliency provided by the air or liquid in the first chamber.

In the present invention, the second chamber of the device is disposed generally adjacent to the first chamber. The chamber having the higher resiliency is positioned generally adjacent to the structure to maximize rigidity for the support device. The chamber having the lower resiliency is positioned so as to be adjacent to the body of the user to provide for the comfort of the user. In this manner, user comfort is maximized while at the same time the necessary amount of support is provided.

In a method embodiment of the present invention, a support device is used to support a body part of a human user. A multi-chamber support device is provided and secured to a structure. The body part of the user is then positioned so as to be in contact with the support device to provide support and comfort to that body part.

It is an object of the present invention to provide a support device having a chamber with a low resiliency which is positioned adjacent to the body of a user to maximize comfort for the user.

It is an object of the present invention to provide a support device which minimizes the amount of fluid required to provide support and comfort to a user.

It is an object of the present invention to provide a multi-chamber support device which contains at least two different fluid media.

These and other objects of the present invention will be more fully understood from the following description of the invention and by reference to the figures and claims appended hereto.

DETAILED DESCRIPTION OF THE INVENTION

As used herein, the physical property "resiliency" has its regular scientific definition, namely the physical property of the capability of a strained body to recover its size and shape after deformation especially caused after compressive stress. The term "resiliency" is used more particularly herein to describe a physical property imparted to a support device by fluid media contained within the support device. Resiliency of a support device therefore correlates to the degree to which reactive forces impact on a user from the surface of a support device when compressive resistance is introduced to the support device by the user. A change in fluids employed in the support device results in a change in the reactive forces generated by the support device when compressive pressure is applied during its use.

As used herein, the term "fluid" includes any substance or various forms and combinations thereof which can be described in the context of its employment in the support device as providing a "resiliency" to the support device. Examples of suitable fluids which are within the scope of this definition include, but are not limited to, air or other gases, liquids with or without components provided therein, gels, block polymers and combinations of these substances. For example, if air is employed as a fluid in the support device of the present invention, then the air will provide resiliency to the support device in the context of the air's containment within the support device. The air, which is a compressible fluid, contained in the support device will generate reactive forces in response to compressive force or resistance applied by a user.

As used herein, the term "structure" is defined as any physical object to which the support device of the present invention can be attached, including but not limited to, an automobile seat, a chair, a helmet or other physical objects employed by a user with which the use of support devices would be desirable.

As used herein, the term "body part" refers to a portion of the body of a living member of the animal kingdom including human beings.

Figure 1:
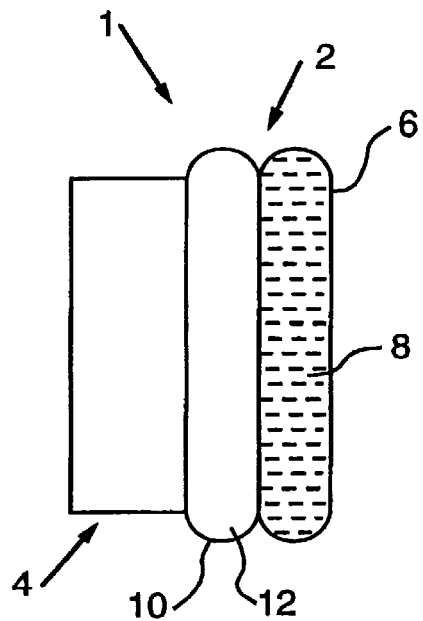
FIG. 1 is a partially schematic sectional view of a support device and structure in accordance with an embodiment of the present invention.

Referring now to FIG. 1, an apparatus 1 of the present invention is shown including a support device 2 secured to a structure 4. The support device 2 is secured to the structure 4 by a suitable, conventional apparatus (not shown) such as mechanical fasteners, adhesives and the like. The support device 2 further comprises a first chamber 6 sealingly containing a first fluid 8 therein. A second chamber 10 is disposed generally adjacent to the first chamber 6 and sealingly contains a second fluid 12 therein. The second chamber 10 can be attached to the first chamber 6 by a suitable, conventional apparatus or method, such as by use of mechanical fasteners, adhesives, and the like. Optionally, the chambers share a common wall (not shown) which forms a portion of each of the individual chambers. The common wall substitutes for the attachment of the first chamber to the second chamber. In addition, the fluids need not completely fill the volume defined by the chambers.

Referring again to FIG. 1, one of the fluids 8, 12 of the chambers 6, 10 is selected from the group consisting of air and liquid. Fluid 8 provides a first resiliency to one chamber 6, and the fluid 12 provides a second resiliency to the other chamber 10. As shown, the second resiliency is higher than the first resiliency. In application of the support device 2 of the present invention, the chamber 10 containing the fluid 12 providing the higher resiliency is positioned generally adjacent to the support structure 4, as shown in FIG. 1, to space the less comfortable but more supportive chamber 10 of the support device 2 a distance away from a user (not shown). The chamber 6 containing the fluid 8 providing the lower resiliency is positioned to be in contact with the body or body portion of the user to maximize comfort for the user and to provide for more effective distribution of forces imposed on the body of the user. The chambers 6, 10 of the support device 2 may have substantially the same volume. Optionally, the volume of one of the chambers has a volume which is greater than the other chamber volume.

Figure 2:
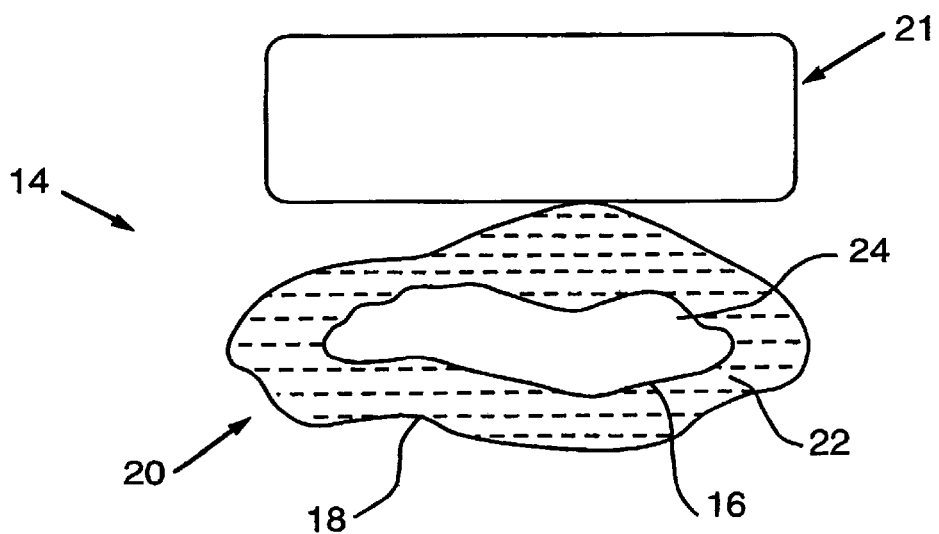
FIG. 2 is a partially schematic sectional view of the support device and structure in accordance with another embodiment of the present invention.

In another embodiment of the present invention shown in FIG. 2, the apparatus 14 includes a support device 20 which has an enclosed chamber 16 contained within a surrounding chamber 18. The surrounding chamber 18 contains a fluid 22 providing a resiliency to the chamber 18 which is lower relative to the resiliency provided by a fluid 24 contained in the enclosed chamber 16. The surrounding chamber 18 is preferably positioned to be closer to the body of a human user (not shown) than the enclosed chamber 16 to maximize the comfort of the user. The surrounding chamber 18 is secured by conventional apparatus such as mechanical fasteners, adhesives, and the like to a structure 21. The fluid 24 contained in enclosed chamber 16 is a fluid providing a relatively higher resiliency than fluid 22 to provide stabilizing capability to the support device 20. The less comfortable enclosed chamber 16 is separated a distance from the user to reduce the potential of detrimental reactive forces generated by the support device 20 on the user.

Referring again to FIG. 2, the surrounding chamber 18 is conventionally vacuum formed into the shape of an elongated bubble having a void formed therein. The void is suitable for receiving the enclosed chamber 16 through an open end formed in the surrounding chamber 18. In a preferred embodiment of the present invention, the enclosed chamber 16 contains air for its fluid while the surrounding chamber 18 contains a viscous liquid or a gel as its fluid. The enclosed chamber may also contain a liquid as its fluid while the surrounding chamber 18 contains various forms of gels or viscous liquids as its fluid. If air is used, the air is preferably under a pressure of more than 0 to about 6 pounds per square inch. It will be appreciated that the embodiment of the present invention shown in FIG. 2 could be employed as a pillow for the head, feet or other body part of a human user.

Figure 3:
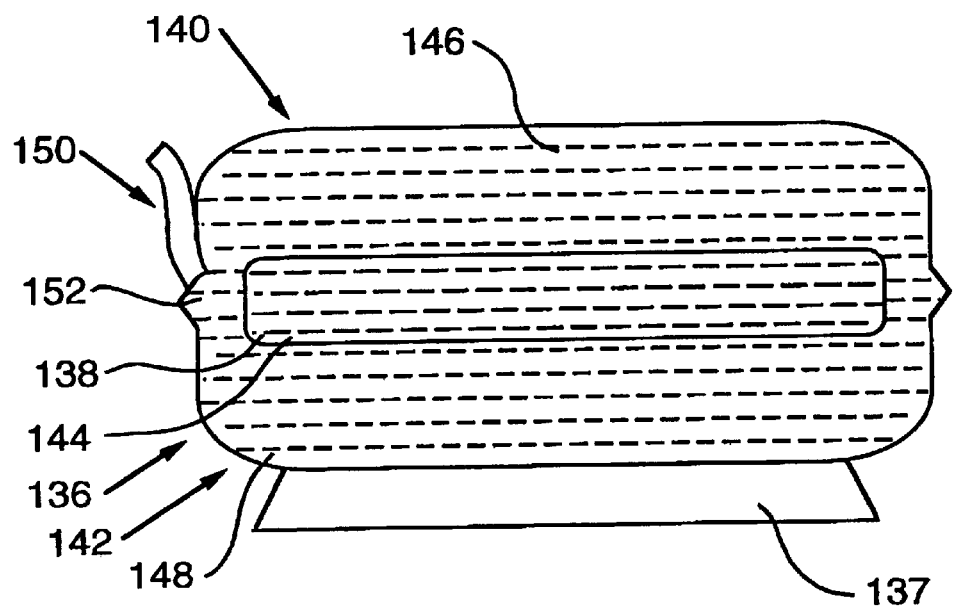
FIG. 3 is partially schematic sectional view of the support device and structure in accordance with another embodiment of the present invention.

Referring now to FIG. 3, in another embodiment of the present invention, a support device 136 is provided with an additional chamber 138 disposed between a first chamber 140 and a second chamber 142. It will be understood that the present invention could also be embodied with one chamber containing a fluid such as air adjacent to another chamber containing a fluid such as a viscous liquid which can be substance known under the trademark SEREFLEX. The additional chamber 138 is substantially entirely filled with fluid and/or with a fully reticulated foam material 144 as shown. The additional chamber 138 provides stability and economical volume to the device 136 while the first and second chambers 140, 142 each respectively contain a fluid 146, 148 which provides lower resiliency to the chambers 140, 142 with respect to the additional chamber 138. The fluids used herein optionally have the same or different viscosities to vary the resiliency provided to the chambers. It is preferable that the first and second chambers 140, 142 overlap each other to cover entirely the additional chamber 138. A conventional valve apparatus 150 can be extended through the overlap portion of the first and second chambers 140, 142 to communicate with a wall portion 152 of the additional chamber 138 to provide for insertion of various fluids into the additional chamber 138.

Referring again to FIG. 3, a conventional air input device (not shown) is optionally employed in conjunction with the valve apparatus 150 to supply the additional chamber 138 with pressurized air or another suitable fluid medium. Thus, the additional chamber 138 can be filled or emptied at the discretion of the user. A gaseous fluid medium such as pressurized air, for example, may be released from the additional chamber 138 through the valve apparatus 150. If a fully reticulated foam material 144 is disposed in the additional chamber 138, then a decrease in environmental pressure in the additional chamber 138 will cause the fully reticulated foam material 144 to expand and fill substantially the entire volume of the additional chamber 138. The fully reticulated foam material 144 provides a relatively high resiliency material which is separated a distance from a user of the support device 136. The support device 136 is preferably connected to a structure 137 which provides a location for attachment and employment of the support device 136 by a user.

In all of the embodiments of the present invention, the wall structure of each of the chambers is preferably resilient. The chambers are formed generally of a closed cell type of plastic composition such as polypropylene, polyethylene or polyurethane and are sufficiently flexible to allow deformation as the user applies pressure to an external surface of the chambers. In addition, the particular thickness of the walls of the chambers must be sufficient to maintain structural integrity when carrying an applied load. The chamber structure provides for increased user comfort when compared with other support devices because of the reduction in reactive forces against the body of the user after prolonged intimate contact.

Additionally, the support device of the present invention must be formed in a manner to be of a comfortable weight. Of significance is the fact that any fluid containment device which must be transported from one area to another should have a low weight in order to allow transportability of the overall cushion system by a user. Liquids such as water, for example, have relatively high densities which will increase the overall weight of the support device, and therefore may not be preferred in all embodiments within the scope of the present invention. In any event, the support device must be adaptable for transportation and use over a wide range of external and environmental conditions since the support device is used in a variety of environments chosen by the user.

In the present invention, the fluids may be liquids which contain a variety of additives which are described herein in further detail. The liquids, with or without additives, are selected from the group consisting of pseudo-liquid, thermoplastic liquid, water, oil, glycerine, liquid plastic, microspheres, emulsions, plasticizers, gels and colloidal suspensions. It will be understood by one skilled in the art that each of these liquids provides a resiliency in its application in the support device of the present invention. The differences among these liquid substances will permit one skilled in the art to provide a variety of fluids having different physical and chemical characteristics which are suitable for use in the support device of the present invention.

An important aspect of the fluids employed in the support device of the present invention is their ability to permit the support device to conform dynamically and continuously to the body contours and micromuscular movements of the user. Such is not possible with conventional air cushions, foam pads, and the like positioned in contact with a user's body because of their compressibility. It will be appreciated that liquids are generally incompressible and this promotes their deformation and adherence to body contours during use.

A low density, deformable gel composition suitable for use in the present invention is disclosed in U.S. Pat. No. 5,475,882, which is hereby incorporated in its entirety by reference. In the present invention, one or more of the chambers can be substantially filled with such a composition or variations thereof.

In addition, the composition can be a fluid which includes a plasticizer or a glycerine and water composition having dispersed therein a plurality of substantially spherically contoured particulates. The particulates have a lower density than the plasticizer composition. The combined plasticizer composition and spherically contoured particulates are formed into a viscous liquid, gel or gel-like overall composition which is maintained within the fluid tight chambers. This gel-like composition is particularly adapted for deformity to the contours of the body of a user, and provides optimization of user comfort. It will appreciated that such a composition is incompressible and therefore well suited for mitigating trauma by absorbing reactive forces when the support device is intimately contoured to the body of a user.

Referring now to FIGS. 4–10, various structures are provided for attachment of the support devices of the present invention. It will be appreciated that a variety of structures could be employed in conjunction with the support device of the present invention, and that FIGS. 4–10 illustrate only some of these structures.

Figure 4:
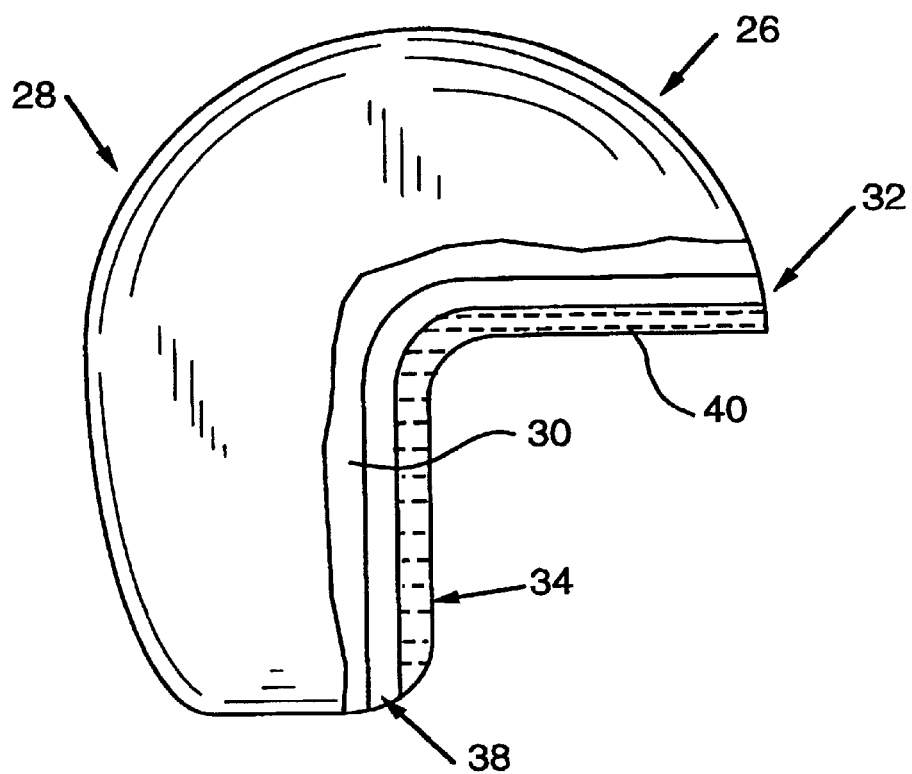
FIG. 4 is a partially sectional view of the support device and structure in accordance with another embodiment of the present invention.

FIG. 4 depicts an embodiment of the apparatus 26 of the present invention in which the structure is a helmet 28 having an interior 30. In this embodiment, the support device 32 is secured to the helmet interior 30. The first chamber 34 of the support device 32 having the fluid 36 providing a lower resiliency is positioned to receive and comfort the head of a user (not shown) wearing the helmet 28. The relatively lower resiliency generated by fluid 36 provides comfortable support to the head of the user. The second chamber 38 is secured to the helmet interior 30 and contains a fluid 40 providing a relatively higher resiliency to provide stability to the support device 32.

Figures 5, 6:
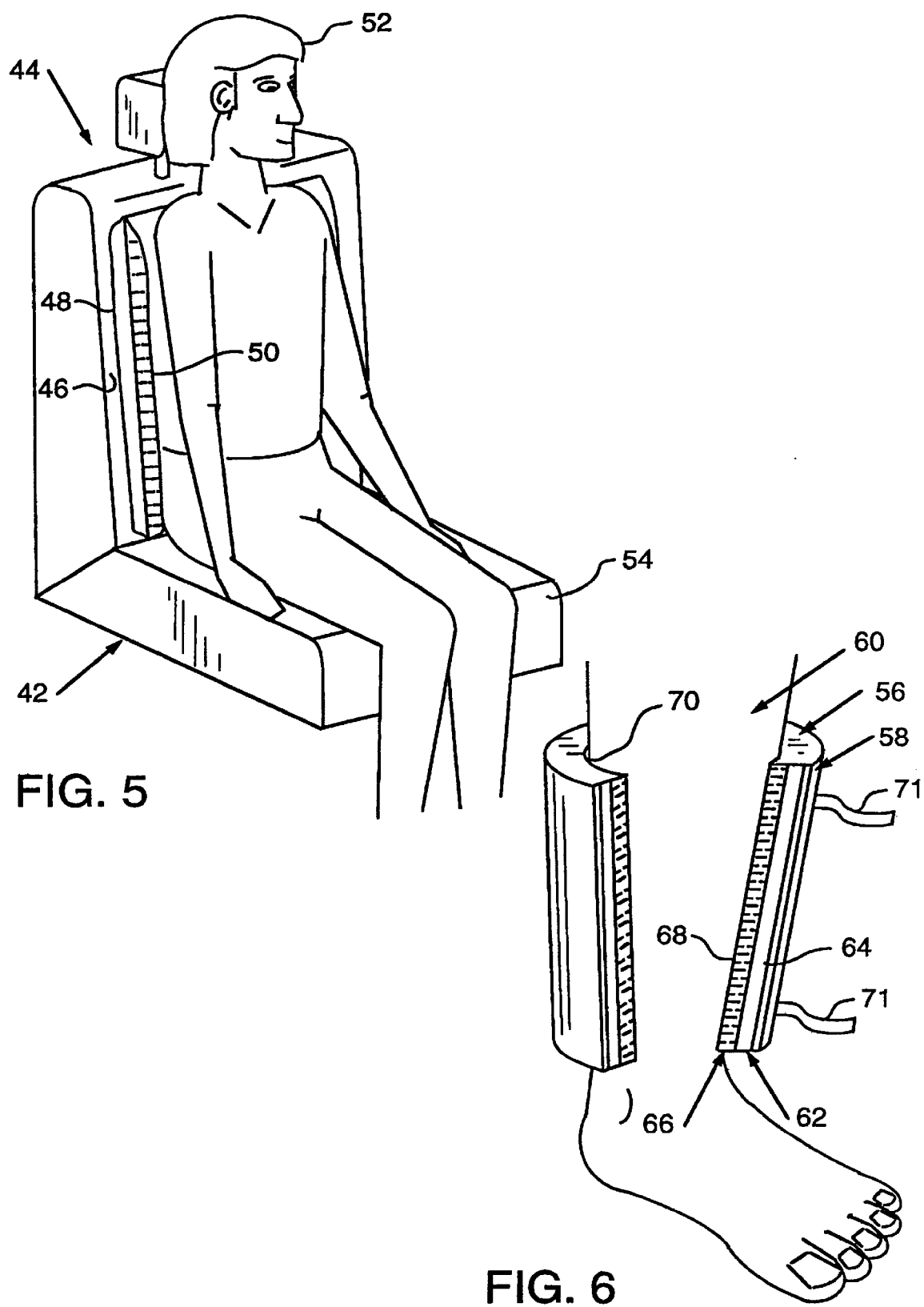
FIG. 5 is an isometric view partially sectioned of the support device and structure in accordance with another embodiment of the present invention.
FIG. 6 is a partially sectional view of the support device and structure in accordance with another embodiment of the present invention.

Referring now to FIG. 5, the structure employed in the present invention is embodied as an automobile seat 42. In this embodiment of the present invention, the support device 44 is preferably secured to at least a portion 46 of the automobile seat 42. The support device 44 is a back support having a structure engaging surface 48 positioned generally adjacent to the automobile seat 42 and a back support surface 50 which is in contact with the back of a user 52. The support device may be a full back support or a partial back support, such as a lumbar back support, for example.

Referring again to FIG. 5, the structure can be a contoured foam structure (not shown) instead of the automobile seat 42 or another structure positioned within the automobile seat 42. The foam structure presents a surface which permits the support device to conform to the foam structure. The support device 44 deforms to the contours of the body or body portion of a user 52 and also presses against the seat 42. The support device can also be positioned inside the automobile seat. The support device could be positioned, for example, so that the chamber having the higher resiliency is secured to a structure such as the frame of the seat. The chamber having the lower resiliency is positioned so as to be closer to the body of a driver sitting in the automobile seat.

FIG. 6 depicts the support device 56 of the present invention secured to a structure such as a cast 58 for supporting the leg 60 of a user. It will be appreciated that other body parts could be similarly supported. In this embodiment, an outer chamber 62 containing a fluid 64 providing a higher resiliency is secured to the cast 58. An inner chamber 66 containing a fluid 68 providing a lower resiliency is secured to the outer chamber 62. The inner chamber 66 provides a surface 70 which is suitable for contact and deformation against the leg 60 of a user. An important aspect of this embodiment is that the inner chamber 66 contains a fluid 68 which maximizes comfort for the user's leg 60 positioned in the leg cast 58.

Referring again to FIG. 6, the higher resiliency outer chamber 62 is partially or substantially filled with a fluid 64 which lends stability to the support device 56. The outer chamber 62 may also be filled with air, which would provide the added benefit of reducing the expense incurred by employing a liquid, for example, in the outer chamber 62 and also reduce the weight of the device. In a preferred embodiment, the outer chamber 62 contains air while the inner chamber 66 contains a gel. A hook and loop arrangement 71, such as one employing a conventional structure sold under the trade designation VELCRO, can be attached to the support device 56 to permit its securement in position around a part of the human anatomy such as the leg or ankle of a user as shown.

Figure 7:
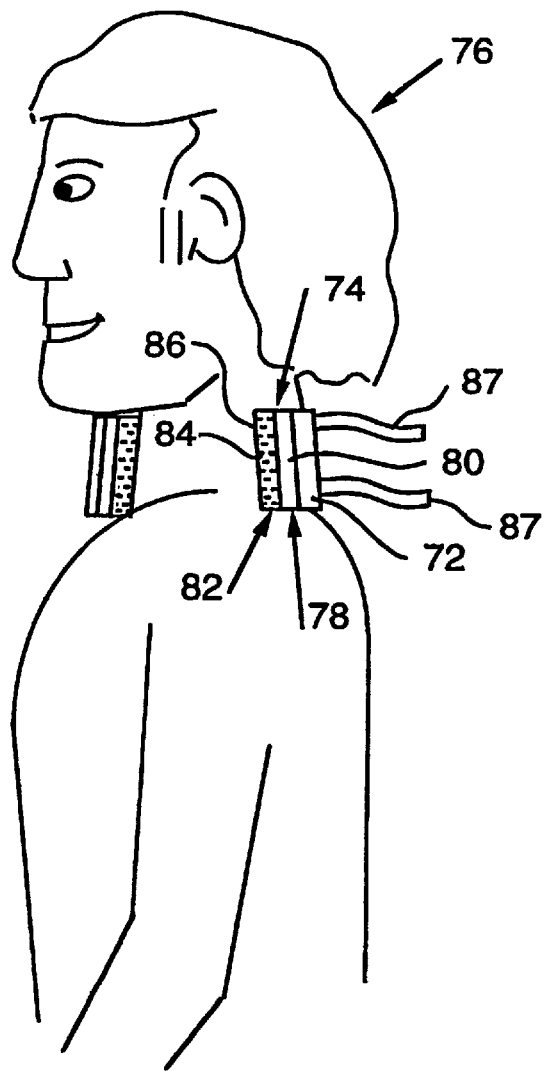
FIG. 7 is a partially sectional view of the support device and structure in accordance with another embodiment of the present invention.

FIG. 7 shows a cervical collar 72 used as the structure to which the support device 74 of the present invention is attached. The cervical collar 72 embodiment is used to support generally head and neck region of a human user 76. An outer chamber 78 containing a fluid 80 providing a higher resiliency is secured to the cervical collar 72. An inner chamber 82 containing a fluid 84 providing a resiliency which is lower relative to the resiliency provided by fluid 80 is secured to the outer chamber 78. The inner chamber 82 provides a surface 86 which is suitable for contact and deformation against the head and neck regions of the user 76. A hook and loop arrangement 87, such as one employing a conventional structure sold under the trade designation VELCRO, can be attached to the support device 74 to permit its securement in position around a part of the human anatomy such as the neck of a user as shown.

Figure 8:
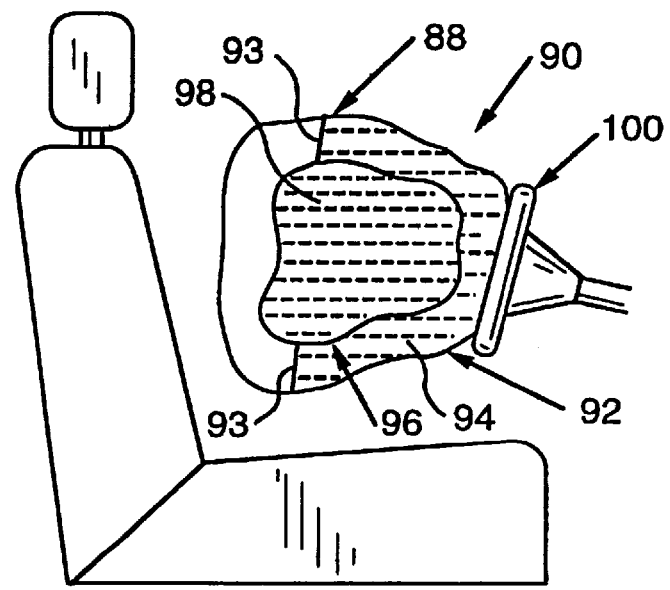
FIG. 8 is a partially sectional view of the support device and structure in accordance with another embodiment of the present invention.

In another embodiment of the present invention shown in FIG. 8, the support device 88 of the present invention is employed with an automobile air bag 90. In this embodiment the surrounding chamber 92 containing the fluid 94 providing a lower resiliency is positioned and secured substantially completely around the higher resiliency enclosed chamber 96 containing the fluid 98. It will be appreciated that the structure of the surrounding chamber 92 must be sufficient to withstand conventional impact force exerted by the air bag 90 against a human user (not shown) when the air bag 90 is activated in an auto accident, for example. The structure of the surrounding chamber 92 must have a structural integrity sufficiently substantial to resist the fluid 94, such as a viscous liquid, from being expelled from the surrounding chamber 92 upon activation of the air bag 90.

Referring again to FIG. 8, the surrounding chamber 92 may have a membrane 93 formed therein to partition the fluid 94 within only a portion of the surrounding chamber 92. It will be appreciated that the support device 88 of the present invention is constructed to assist the lower resiliency chamber 92 fluid 94 in safely impacting the human user during operation of the air bag 90. It will also be appreciated that the air bag could be provided in generally adjacent layers, with the higher resiliency chamber sandwiched between the outer lower resiliency chamber and the steering column. It is preferred that a viscous liquid such as one sold under the trademark SEREFLEX be used on the impact area of the support device.

Figure 9:
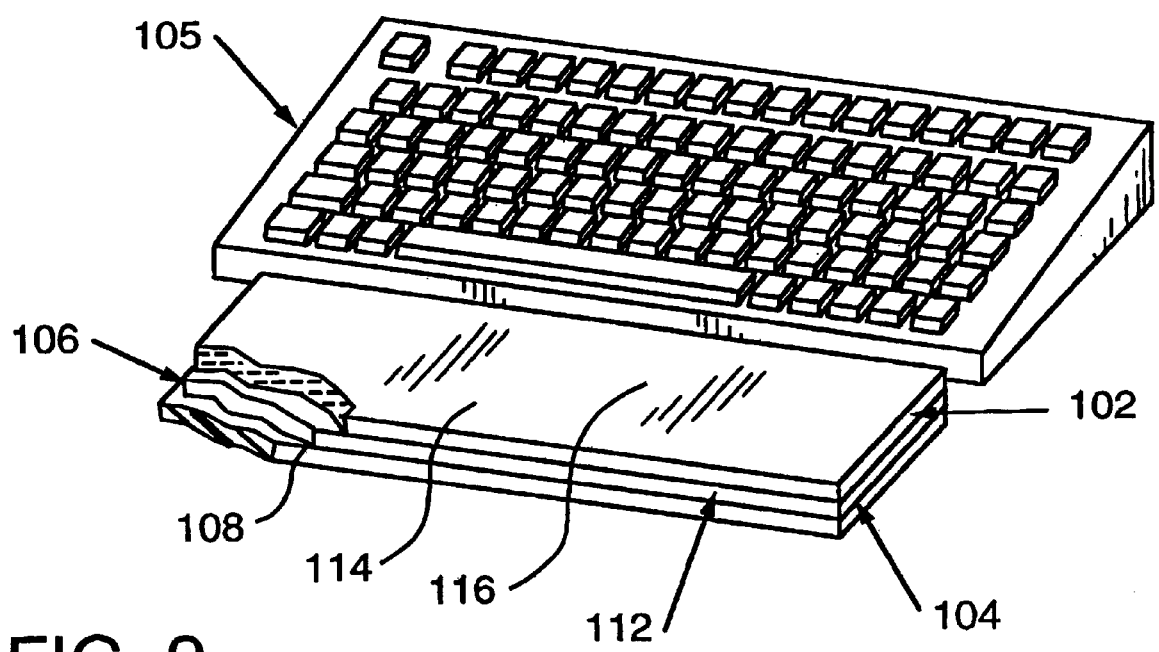
FIG. 9 is a partially sectional view of the support device and structure in accordance with another embodiment of the present invention; and, FIG. 10 is a partially sectional view of the support device and structure in accordance with another embodiment of the present invention.
Figure 10:
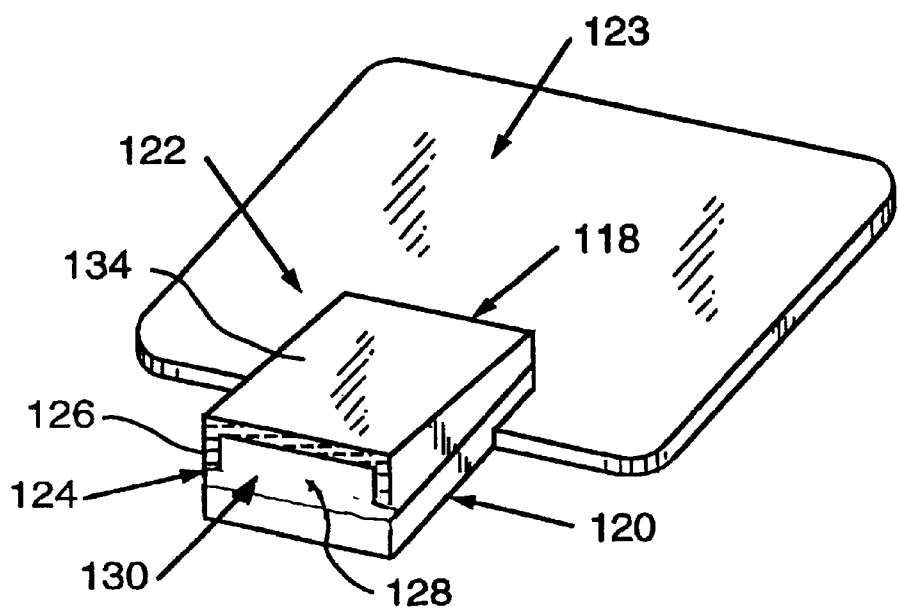

FIGS. 9 and 10 depict embodiments of wrist supports of the present invention.

Referring now to FIG. 9, the support device 102 of the present invention is secured to a base 104 in its employment to maintain and support the hand and wrist regions of a user (not shown) when using a keyboard 105. The first chamber 106 containing the fluid 108 providing a higher resiliency is attached to the base 104. The second chamber 112 containing the fluid 114 providing the lower resiliency is secured to the first chamber 106 and presents a deformable surface 116 suitable for intimate contact with the hand and wrist regions of a user operating the keyboard 105. The first chamber 106 is filled with a fluid 108 such as air, for example, to minimize use of viscous liquid in the second chamber 112 of the support device 102 and to maximize stability for the support device 102. In this embodiment, the base 104 is positioned generally adjacent to the keyboard 105.

Referring now to FIG. 10, in another embodiment of the present invention, the support device 118 of the present invention is secured to a base 120 to provide a mouse pad support 122 for use with a mouse pad 123. A surrounding chamber 124 is secured in a suitable, conventional manner to the enclosed chamber 130 of the mouse pad support 122. The surrounding chamber 124 contains a fluid 126 providing a resiliency which is lower than the resiliency provided by a fluid 128 contained in an enclosed chamber 130. The enclosed chamber 130 is partially surrounded by the surrounding chamber 124 to maximize stability for the mouse pad support 122 while reducing the amount of fluid 126 needed to be contained in the surrounding chamber 124. The enclosed chamber 130 is preferably connected to the base 120 by a suitable mechanical means.

It will be appreciated that all of the particular embodiments described above, as well as other embodiments of the present invention comprising a support device attached to a structure, can employ a support device having two adjacent chambers, as generally shown in FIG. 1, or a support device in which one chamber is contained within the other chamber, as generally shown in FIG. 2.

In a method embodiment of the present invention, a method of using a support device to support a body part is disclosed. The first step is providing a support device which comprises a first chamber containing a first fluid positioned generally adjacent to a second chamber containing a second fluid. The fluid in one of the chambers is selected from the group consisting of air and liquid. The second fluid provides a resiliency which is higher or lower than the resiliency provided by the first fluid.

Next, a structure is provided to which the support device is secured. The chamber containing the fluid providing the higher resiliency is positioned next to the structure to maximize the stability of the support device. Then, a body part of a human user is positioned in contact with the lower resiliency fluid chamber to support the body part in a comfortable manner. Thus, the chamber having the lower resiliency is preferably positioned closer to the body of the user than the other chamber. The method can be employed with a helmet having an interior by securing the support device to the interior of the helmet and then positioning the head of the user in contact with the support device. Other structures which are used in the method may include an automobile seat, a cast, wrist supports, sleeping pillows, heel supports, elbow supports, and other pressure sensitive portions of the human anatomy.

The method may also include providing the chambers as substantially continuous and employing a support device which has a support engaging surface and a back support surface for supporting the back of the user. The method may also include employing a suitable, conventional valve apparatus positioned on a chamber of the support device which has air, for example, as its fluid medium so as to make this air chamber inflatable or deflatable based upon the preference of the user. The method employs a valve apparatus which is standard in the art. The valve apparatus can be a standard plug valve known in the art to allow the insertion and containment of fluid within the chamber. Once fluid is inserted within the chamber, the plug valve is closed to maintain the fluid internally within the chamber.

Whereas particular embodiments of this invention have been described above for purposes of illustration, it will be evident to those skilled in the art that numerous variations of the details of the present invention may be made without departing from the invention as defined in the appended claims.

What is claimed is:

1. An apparatus comprising a support device secured to a structure, said support device comprising:

a first chamber containing a first fluid; and, a second chamber, disposed generally adjacent to said first chamber, containing a second fluid, wherein the fluid in one of said chambers provides a first resiliency, the fluid in the other of said chambers provides a second resiliency different from said first resiliency, and said support device secured to said structure so that in normal use said chamber having the lower resiliency is positioned closer to the body of a user than the other of said chambers.

2. The apparatus of claim 1, wherein at least one of said fluids is a gel.

3. The apparatus of claim 2, wherein said gel is a low density, deformable gel composition.

4. The apparatus of claim 1, wherein said fluid is selected from the group consisting of pseudo-liquid, thermoplastic liquid, water, oil, glycerine, liquid-plastic microspheres, emulsions, plasticizers, and colloidal suspensions.

5. The apparatus of claim 1, wherein said fluid in said higher resiliency chamber is air.

6. The apparatus of claim 5, wherein said air is under a pressure of no more than about 6 pounds per square inch.

7. The apparatus of claim 1, wherein one of said chambers is contained within the other of said chambers.

8. The apparatus of claim 7, wherein said contained chamber contains air and the other of said chambers contains a liquid.

9. The apparatus of claim 7, wherein said contained chamber contains a fluid and the other of said chambers contains a gel.

10. The apparatus of claim 9, wherein said fluid is a gel providing a resiliency different than the resiliency provided by said contained gel.

11. The apparatus of claim 1, wherein each of said chambers has substantially the same volume.

12. The apparatus of claim 1, wherein one of said chambers has a greater volume than the other of said chambers.

13. The apparatus of claim 1, wherein said chambers are substantially continuous, and said support device has a first surface secured to said structure and a second surface in contact with a body part of the user being supported.

14. The apparatus of claim 1, wherein said structure is selected from the group consisting of a back support, an automobile seat, a helmet, a cast, a cervical collar, an automobile air bag, and a wrist support.

15. The apparatus of claim 1, further comprising an additional chamber positioned between said first and second chambers.

16. The apparatus of claim 15, further comprising a layer of fully reticulated foam disposed in said additional chamber.

17. The apparatus of claim 16, further comprising a valve means in communication with said additional chamber for pressurizing and depressurizing said additional chamber with a gas or fluid, thereby expanding and contracting said reticulated foam in response to actuation of said valve means.

18. A method of using a support device with a structure to support a body part comprising:

providing a support device comprising a first chamber containing a first fluid, and a second chamber, disposed generally adjacent to said first chamber, containing a second fluid, wherein the fluid in one of said chambers provides a first resiliency and the fluid in the other of said chambers provides a second resiliency different from said first resiliency;

securing said support device to said structure; and, positioning a body part in contact with said support device so that said chamber having the lower resiliency is closer to the body of a user than the other of said chambers.

19. The method of claim 18, including employing a helmet having an interior as said structure, securing said support device to said interior, and positioning the head of a user in contact with said support device.

20. The method of claim 18, including employing an automobile seat as said structure.

21. The method of claim 18, including providing said chambers as substantially continuous, and employing a support device having a structure engaging surface and a back support surface to support at least a portion of the back of a user.

22. The method of claim 18, including employing a cast as said structure.

23. The method of claim 18, further including employing a valve means positioned on said chamber having air as said fluid to make said air chamber inflatable or deflatable.

* * * * *